United States Patent [19]

Jaffe et al.

[11] 4,448,058

[45] May 15, 1984

[54] RESPIRATORY GAS ANALYSIS INSTRUMENT HAVING IMPROVED VOLUME CALIBRATION METHOD AND APPARATUS

[75] Inventors: Michael B. Jaffe; Charles R. Luper, both of Anaheim; Eric Mabry, Westminster; Howard J. Reid, Brea, all of Calif.

[73] Assignee: Sensormedics Corporation, Anaheim, Calif.

[21] Appl. No.: 394,608

[22] Filed: Jul. 2, 1982

[51] Int. Cl.$^3$ ............................................. G01N 31/00
[52] U.S. Cl. ........................................ 73/23; 73/1 G; 128/719; 364/571
[58] Field of Search .................. 73/23, 1 G; 128/719; 422/84; 436/900; 364/571, 497

[56] References Cited

U.S. PATENT DOCUMENTS 3,948,604  4/1976  Hoppesch ............................ 73/1 G
4,178,919  12/1979  Hall ..................................... 422/84
4,316,380  2/1982  Heim et al. .......................... 73/23

FOREIGN PATENT DOCUMENTS 2950746  6/1981  Fed. Rep. of Germany ........ 422/84

Primary Examiner—Stephen A. Kreitman
Attorney, Agent, or Firm—Lyon & Lyon

[57] ABSTRACT

An improved gas volume calibration method and apparatus for use in respiratory gas analyzers. A control unit monitors the flow of calibration gas through the analyzer by monitoring the electrical signals produced by a gas turbine and a breath switch. During calibration, a known volume of calibration gas is repeatedly delivered to the analyzer from a calibration syringe at each of a number of different flow rates. On the basis of the information received from the turbine and the breath switch, the control unit generates and stores a piecewise linear approximation of the nonlinear characteristic of the turbine. This stored turbine characteristic is then made available during subsequent measurements to eliminate those volume errors which are associated with variations in the rate at which the sample gas is delivered, thereby affording measurements of improved accuracy.

50 Claims, 8 Drawing Figures (1) $b'_B = b_B \cdot F_{CB}$ (2) $F_{CB} = \dfrac{1}{1 + \dfrac{P_{B\,CALC} - P_{B\,MEAS}}{P_{B\,CALC}}}$

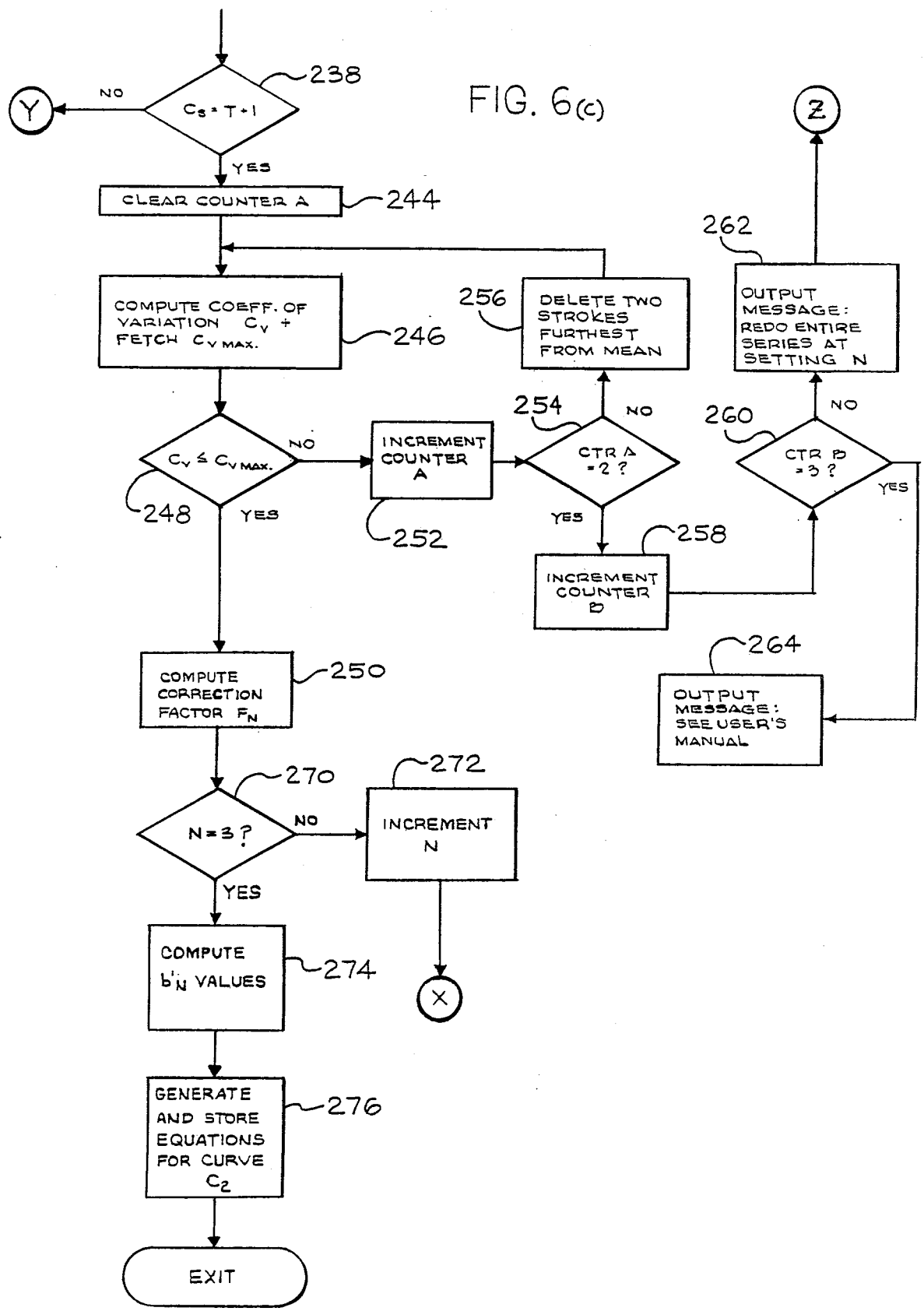

RESPIRATORY GAS ANALYSIS INSTRUMENT HAVING IMPROVED VOLUME CALIBRATION METHOD AND APPARATUS

BACKGROUND OF THE INVENTION

In calibrating respiratory gas analysis instruments, it has long been the practice to supply the instrument with a pulsatile flow of calibration gas (usually air) from a device known as a calibration syringe. This syringe typically includes a piston and cylinder arrangement which pumps gas into the instrument, through a check valve, as the operator moves the piston between first and second positions. Because the cylinder has a volume comparable to the volume of gas that is exhaled during a typical human breath, and because the ejection stroke of the piston has approximately the same duration as an exhaled breath, the calibration syringe allows the instrument to be calibrated under conditions that simulate those which exist when the instrument is later used with a test subject.

The use of known volume calibration syringes and procedures has been found to result in sizable errors in the volume of gas delivered during calibration. One cause of this error, known as "siphoning", results from the fact that the inertia of the gas flowing through the check valve has a tendency to open the check valve when the piston reaches the end of its stroke. Such siphoning affects the accuracy of the calibration process by causing the actual volume of gas supplied to the instrument to exceed the volume of the calibration syringe.

Another error that is associated with the use of manually operated calibration syringes results from the fact that, due to operator inattention, the piston may not be moved between exactly the same beginning and end positions during each ejection stroke. An operator may, for example, not withdraw the piston to its true outermost position, or may not push the piston to its true innermost position. Any such deviations from the desired inner and outer positions affect the volume of gas delivered by the syringe during calibration and, therefore, the accuracy of all measurements that are based on that calibration.

Another even larger error that is associated with the use of manually operated calibration syringes is the error that results from the nonlinearity of the response of the gas turbine. This nonlinearity can cause the number of output pulses that are produced by the turbine during the flow of a known volume of calibration gas to vary substantially, depending upon the rate at which the gas is delivered. The difficulty is that most operators have difficulty in operating the syringe in a consistent manner. As a result the number of turbine output pulses produced during an ejection stroke of the syringe will vary randomly from stroke to stroke. In the past this nonlinearity has been dealt with by introducing a flow of a "bias" gas which causes the rate of gas flow through the turbine to remain in a range of values within which its response is relatively flat. This approach, however, only partially solves the problem. It does not actually eliminate variations in the turbine output with variations in the rate of flow therethrough. In any case, the use of bias gas flows is expensive since it requires the establishment of an additional accurately controlled gas flow, and since the gas flow paths through the instrument are more complex than they would be in the absence of a bias gas flow.

SUMMARY OF THE INVENTION

In accordance with the present invention, there is provided an improved method and apparatus for calibrating a respiratory gas measuring instrument which is not subject to the above-described problems and which affords high gas volume calibration accuracy without requiring the use of bias gas flows.

The present invention provides a method and apparatus by which data received from a gas turbine and a breath switch during calibration are used to produce a nonlinear characteristic curve for the turbine. The resulting characteristic curve is made available for use during the taking of measurements to provide corrected gas volume data that takes into account the duration and rate of flow of each breath. Because measurements of the concentration of the gaseous components of breath are strongly affected by the volume thereof, the gas concentration readings which are based on this corrected volume data have an accuracy better than that available prior to the present invention.

In accordance with another feature of the present invention, the instrument is arranged to prompt the operator who calibrates it, and thereby lead him through the volume calibration process in a way that assures that the latter is properly performed. In the event that any of the steps of the volume calibration process are improperly performed, the instrument will reject the resulting faulty data and inform the operator of what he must do to provide acceptable data. Once an acceptable set of data is available, the instrument automatically produces a piecewise linear approximation of the non-linear characteristic of the turbine and stores the same for use during subsequent measurements.

In spite of the sophisticated nature of the calibration system of the invention, the calibration process itself is, from the operator's standpoint, quite simply and conveniently performed. As a result, it is practical to volume calibrate the instrument daily or even before each series of measurements. Such frequent calibrations are desirable because the characteristics of a turbine can change with wear and with the accumulation of dirt on the blades or bearings. Thus, the volume calibration method and apparatus of the invention assures that the instrument always has available to it volume data which reflects the current condition of the turbine.

Generally speaking, the calibration system of the present invention contemplates the storage of a piecewise linear approximation of the nonlinear characteristic of a typical gas turbine of the type used in the instrument. Each of the linear segments of this characteristic represents a particular range of turbine pulses per unit volume of calibration gas as a function of the rate at which that gas is delivered. On the basis of the turbine output data that is gathered as the operator manually operates the syringe, the instrument generates a correction factor for each piecewise-linear segment. When all of these correction factors are available, the instrument then generates a corrected piecewise linear approximation of the characteristic curve of the actual turbine. The latter characteristic is then stored for use during the taking of measurements. As a result of the availability of this nonlinear approximation of the actual turbine characteristic, the instrument is able to provide accurate concentration readings, in spite of changes in the rate at which the test subject breaths.

DESCRIPTION OF THE DRAWINGS

Further objects and advantages of the present invention will be apparent from the following description and drawings in which.

DESCRIPTION OF THE PREFERRED EMBODIMENT

Figure 1:
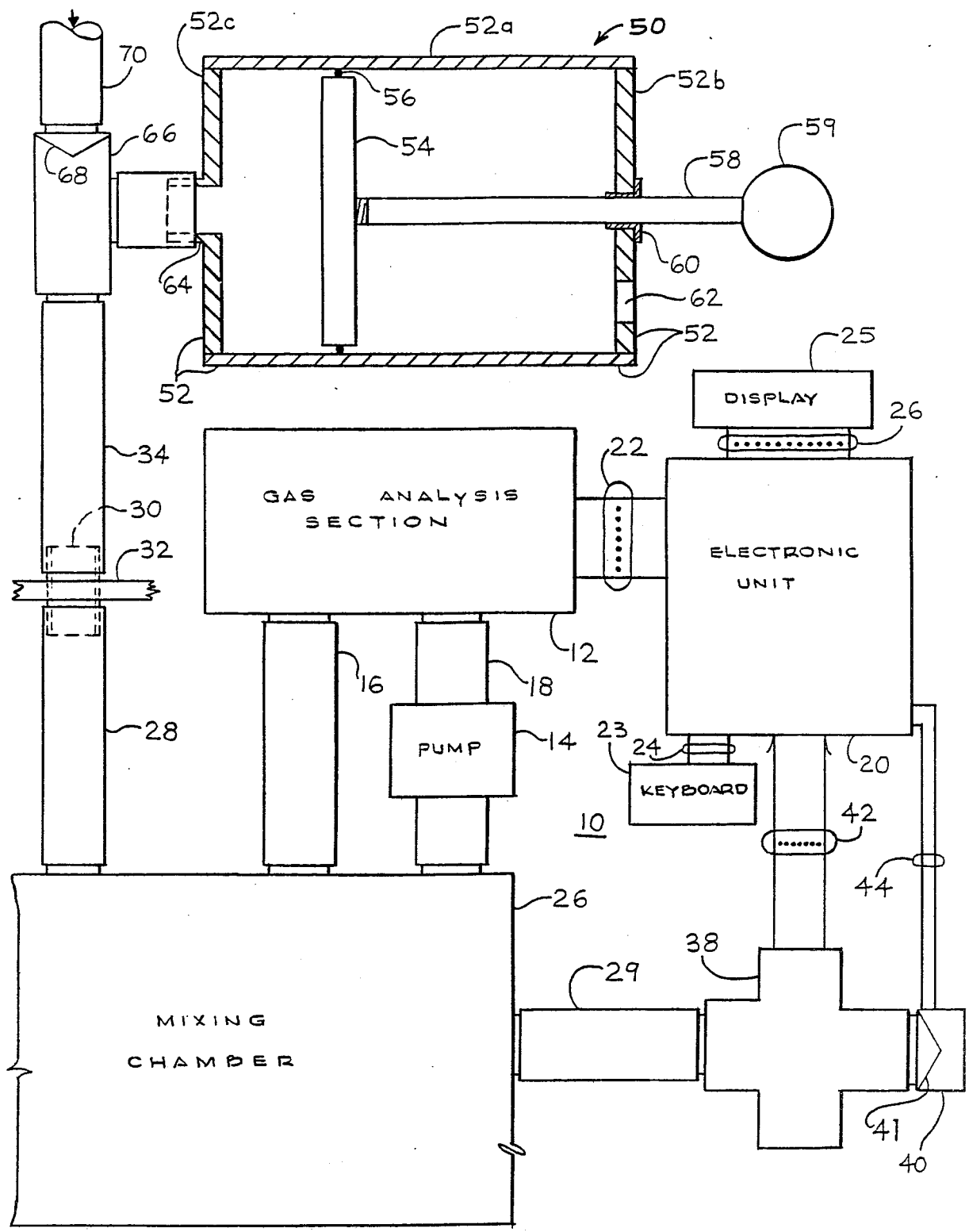
FIG. 1 is a block diagram of a respiratory gas analysis instrument, shown with the connections which exist during volume calibration, including a known type of calibration syringe.

Referring to FIG. 1, there is shown a block diagram of a respiratory gas analysis instrument 10 which is shown with the connections which exist during volume calibration. Instrument 10 includes a gas analysis section 12 which may comprise one or more gas analyzers such as, for example, nondispersive infrared gas analyzers. For measurements on human breath these analyzers will typically include one analyzer that is sensitive to the concentration of oxygen and another that is sensitive to the concentration of carbon dioxide. The sample gas that is measured by these analyzers is circulated through analysis section 12 by a pump 14 which drives the sample gas through the path including an inlet line 16 and an outlet line 18.

The instrument of FIG. 1 also includes an electronic control unit 20 which is connected to analysis section 12 through a plurality of electrical conductors 22, to a keyboard 23 through a set of electrical conductors 24, and to an operator-readable display 25 through a set of electrical conductors 26. Control unit 20 may include electronic circuitry of either the hard-wired type or the microcomputer-controlled type, although the latter are preferred because of their greater cost effectiveness.

The gas to be measured is supplied to analysis section 12 from a mixing chamber 26 which is provided with an inlet line 28 and an outlet line 29. In order to facilitate the connection of inlet line 28 to either a source of sample gas or a source of calibration gas, inlet line 28 preferably terminates at one end of a connector 30 that is mounted on an interface panel 32. The other end of connector 30 is thereby made available for coupling to the desired sample or calibration gas source. In FIG. 1 connector 30 is connected to a line 34, which leads to a source of calibration gas, namely: volume calibration syringe 50.

In order that control unit 20 may monitor the volume and rate of flow of the gas flowing out of mixing chamber 26, there is provided a gas turbine 38, which is connected to control unit 20 through a set of electrical conductors 42, and a combination check valve and breath switch 40, which is connected to control unit 20 through a set of electrical conductors 44. Gas turbine 38 is preferably of a known type that includes turbine blades, not shown, which are arranged to rotate as gas flows thereover. These blades are ordinarily arranged to interrupt the beams of light which a plurality of LED's direct against a plurality of respective phototransistors to produce a multi-phase set of output pulses on conductors 42. Thus, turbine 38 supplies to control unit 20, over conductors 42, a train of pulses the number and frequency of which varies in accordance with the volume and rate of flow of gas flowing therethrough.

Combination check valve-breath switch 40, which may be of a known type, preferably includes a check valve 41 which is gently biased in its closed position to assure that gas enters mixing chamber 26 only through inlet line 28. Device 40 also includes a breath switch (not shown) which assumes a first state when valve 41 is open, and a second state when valve 41 is closed. Because of the cyclic nature of breath, the openings and closings of the breath switch mark the beginnings and endings of breaths. The state of the breath switch is monitored by control unit 20, through conductors 44, to enable it to interpret the concentration readings from gas analysis section 12. In particular, by counting the number of pulses received from the gas turbine during the time that the breath switch is open, the volume of each breath is determined so that it may be used in interpreting the concentration readings provided by gas analysis section 12.

Because the response of a gas turbine is known to be nonlinear, it has been the practice, prior to the present invention, to maintain a flow of bias gas through a turbine and thereby maintain the latter within a relatively flat portion of its operating characteristic. The provision of an accurately regulated source of such bias gas is, however, relatively costly. Moreover, because of the nonlinearities associated with the mixing of the sample and bias gases, as well as the residual slope of the turbine characteristic, such an approach is relatively inaccurate. In accordance with one feature of the present invention, the use of a bias gas flow is eliminated and the nonlinear response of turbine 38 is dealt with by calibrating instrument 10 at a variety of different gas flow rates and thereby providing it with the ability to derive accurate volume data from turbine 38 in spite of fluctuations in the rate of gas flow therethrough. In this manner the instrument as a whole is made able to provide measurements of improved accuracy over a wide range of sample flow rates.

In particular, in calibrating instrument 10 in accordance with the present invention, control unit 20 takes a previously stored piecewise linear approximation of the nonlinear characteristic of a representative turbine of the type being used, and combines the same with turbine data that is produced as an operator directs an accurately known volume of gas through the turbine at a plurality of different flow rates. This gas is supplied through the use of an improved volume calibration syringe that reduces operator-related volume errors. Based on the data received, control unit 20 produces and stores a corrected piecewise linear approximation that reflects the nonlinear response of the actual gas turbine then being used. Illustrative ones of these piecewise linear approximations of representative and individual turbine characteristics are shown as "curves" C1 and C2, respectively, of FIG. 2, which will be described in detail later. The calibration method and apparatus by which this desirable result is accomplished enables the instrument to operate with high accuracy at a variety of sample gas flow rates not only after its initial calibration, but also after each of any number of subsequent calibrations. In this manner the benefits of the invention are preserved in spite of those changes in turbine characteristics that are associated with wear, the accumulation of dirt and other factors.

In the upper portion of FIG. 1, there is shown a volume calibration syringe 50 of a type that is known in the art. This syringe includes a housing 52 having a cylindrical section 52a, a first end plate 52b, and a second end plate 52c. Slidably mounted within housing 52 is a piston 54 which is sealed to the inner surface of cylindrical section 52a by a suitable O-ring 56. Piston 54 is driven manually by means of a shaft 58, having a knob-shaped handle 59, which is slidably mounted on end plate 52b by a bushing 60. The partial vacuum that tends to arise behind the trailing surface of piston 54 during the ejection stroke thereof is relieved by the in-flow of ambient air through an aperture 62 in end plate 52b.

The gas that is ejected from syringe 50 by the forward movement of piston 54 flows through an outlet nipple 64 which is coupled to a T-connector 66. The latter connector includes a check valve 68 which permits gas to flow inwardly through atmospheric inlet line 70, but not in the reverse direction. During the intake stroke of piston 54, check valve 68 opens to admit ambient air (the calibration gas) to syringe 50. Under this condition, check valve 41 is closed, preventing syringe 50 from drawing gas from mixing chamber 26. During the ejection stroke of syringe 50, check valve 68 closes, forcing the ejected air to flow into mixing chamber 26 through lines 34 and 28. Under this condition, check valve 41 opens to vent to the atmosphere the gas that is displaced from mixing chamber 26. Thus, as piston 54 is repeatedly moved between its first or outermost position and its second or innermost position, mixing chamber 26 is provided with a pulsatile flow of calibration gas which is similar in quantity and character to that produced by a test subject. It will be understood that ambient air is a desirable calibration gas because of the fact that it is the change which the cardiopulmonary system of the test subject produces on ambient air which is of interest to the user of instrument 10.

One source of error that is associated with the use of the calibration syringe of FIG. 1 is a volume error that is caused by the inertia of the gas that flows in line 34 during an ejection stroke. This gas flow tends to open check valve 68 after piston 54 reaches the end of its stroke. This opening of the check valve is known as "siphoning" and causes the volume of gas flowing through the instrument to exceed the actual volume of the syringe.

Another operator-related source of error is associated with the occurrence of incomplete strokes, such as those resulting from failure of an operator to move piston 54 between its true outermost and innermost positions during each ejection stroke. Such incomplete strokes naturally cause the volume of gas that is caused to flow through the instrument to be less than the full volume of the syringe.

The most important operator-related error that is associated with the use of the calibration syringe of FIG. 1, however, is the volume error that results from moves piston 54 during a series of ejection strokes. This error occurs because different stroke speeds cause turbine 38 to operate at different regions of its non-linear characteristic. Operation at these different regions in turn causes a known volume of calibration gas to produce different numbers of turbine output pulses. In the absence of a procedure for dealing with the different apparent volumes that are associated with different numbers of turbine output values, such differences result in volume uncertainties and errors.

In accordance with the present invention, there is provided an improved method and apparatus for calibrating the instrument of FIG. 1 at gas flow rates that correspond to a number of different regions of the non-linear operating characteristic of its turbine, and thereby enabling the instrument to determine the volumes of gas that are later delivered at any of those flow rates. In addition, for each of the plurality of flow rates at which the instrument is calibrated, the invention imposes criteria for the acceptance or nonacceptance of the turbine data that is produced by the operation of the syringe, thereby assuring that only ejection strokes that meet predetermined minimum standards are used in the calibration process. Finally, the present invention contemplates improvements to the calibration syringe itself, which improvements eliminate the above-mentioned siphoning problem and facilitate the establishment of a number of different calibration gas delivery rates. Together these improvements greatly improve the accuracy of the calibration of the instrument and thereby improve the accuracy of all of the subsequent measurement that are based thereon.

Figure 3:
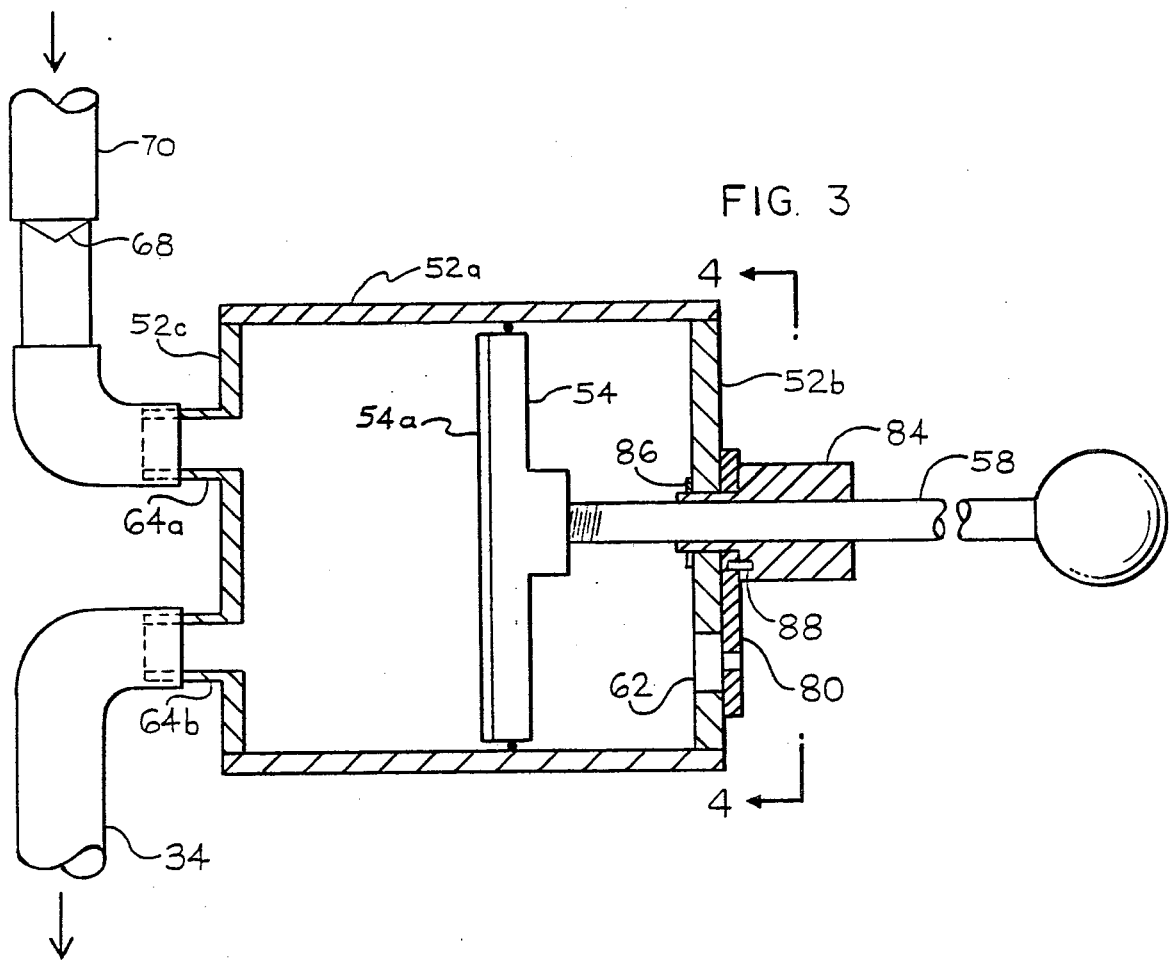
FIG. 3 is a cross-sectional view of an improved volume calibration syringe constructed in accordance with the present invention.
Figure 4:
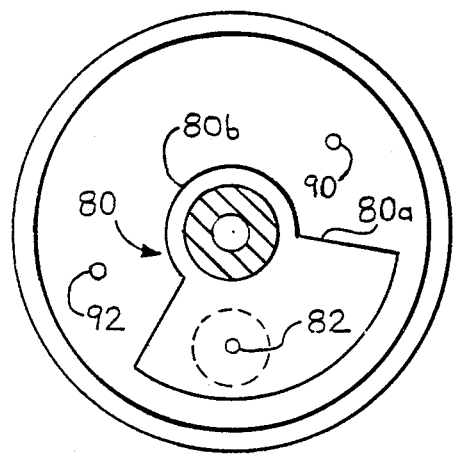
FIG. 4 is a cross-sectional view taken along the line 4—4 of FIG. 3.

To the end that the above-mentioned siphoning problem may be eliminated, the preferred embodiment of the present invention includes an improved gas volume calibration syringe 50' shown in FIGS. 3 and 4. The syringe of FIG. 3 is in some respects similar to that of FIG. 1, like functioning parts being similarly numbered, but differs therefrom in several important respects. The first of these is that, in the syringe of FIG. 3, end plate 52c is modified to provide separate inlet and output nipples 64a and 64b, respectively. Associated with this difference is the elimination of T-connector 66 of FIG. 1 and the connection of a check valve 68 in series with line 70. Finally a flat rubber covering 54a is attached to the leading edge of piston 54. Together these modifications eliminate the above-described siphoning problem. This is because, when piston 54 reaches the end of its stroke, rubber covering 54a makes contact with the inner surface of second end plate 52c, thereby suddenly cutting off the flow of gas in lines 70 and 34. As a result of this positive shut-off, no additional gas can enter chamber 26 after the end of a stroke.

A second improvement in syringe 50' of FIG. 3 results from the provision therein of a control plate 80 which allows an operator to selectably control the rate at which air can flow into syringe through end plate aperture 62. As is most clearly seen in FIG. 4, control plate 80 includes a sector-shaped section 80a, which is provided with one or more flow-limiting holes such as 82, and a circular section 80b which is centered on shaft 58. In the preferred embodiment, control plate 80 is held against the outer surface of end plate 52b by being sandwiched between that end plate and a control member 84 which is rotatably fastened to plate 52b by a suitable retaining washer 86. A pin 88 which fits into control plate 80 and control member 84 assures that these two elements rotate as a unit, thereby allowing plate 80 to be conveniently positioned by grasping and turning the end of member 84.

When control plate 80 is rotated to its counterclockwise limit, which may be defined by the position of a stop pin 90, aperture 62 is not blocked by plate 80 and therefore allows gas to flow into the rear of syringe 50' at a high rate. Under this condition, the syringe may be stroked rapidly, resulting in the delivery of calibration gas at relatively high rates. When, on the other hand, plate 80 is rotated so that hole 82 is aligned with aperture 62, the rate at which gas can flow into the rear of syringe 50' is greatly reduced. The effect of this flow rate reduction is to slow down the ejection stroke of syringe 50 and thereby reduce the delivery rate of calibration gas. Finally, when control plate 80 is rotated to its clockwise limit, which may be defined by the position of stop pin 92, aperture 62 is substantially blocked by control plate 80, thereby limiting the rate at which gas can flow into the rear of syringe 50' to the rate at which gas can leak through the clearance space between plates 80 and 52b. Under this condition, strokes can be completed only slowly, resulting in a low gas delivery rate. It will therefore by seen that, for a given amount of stroke force by an operator, the syringe of FIG. 3 establishes three different delivery rates for calibration gas.

Figure 2:
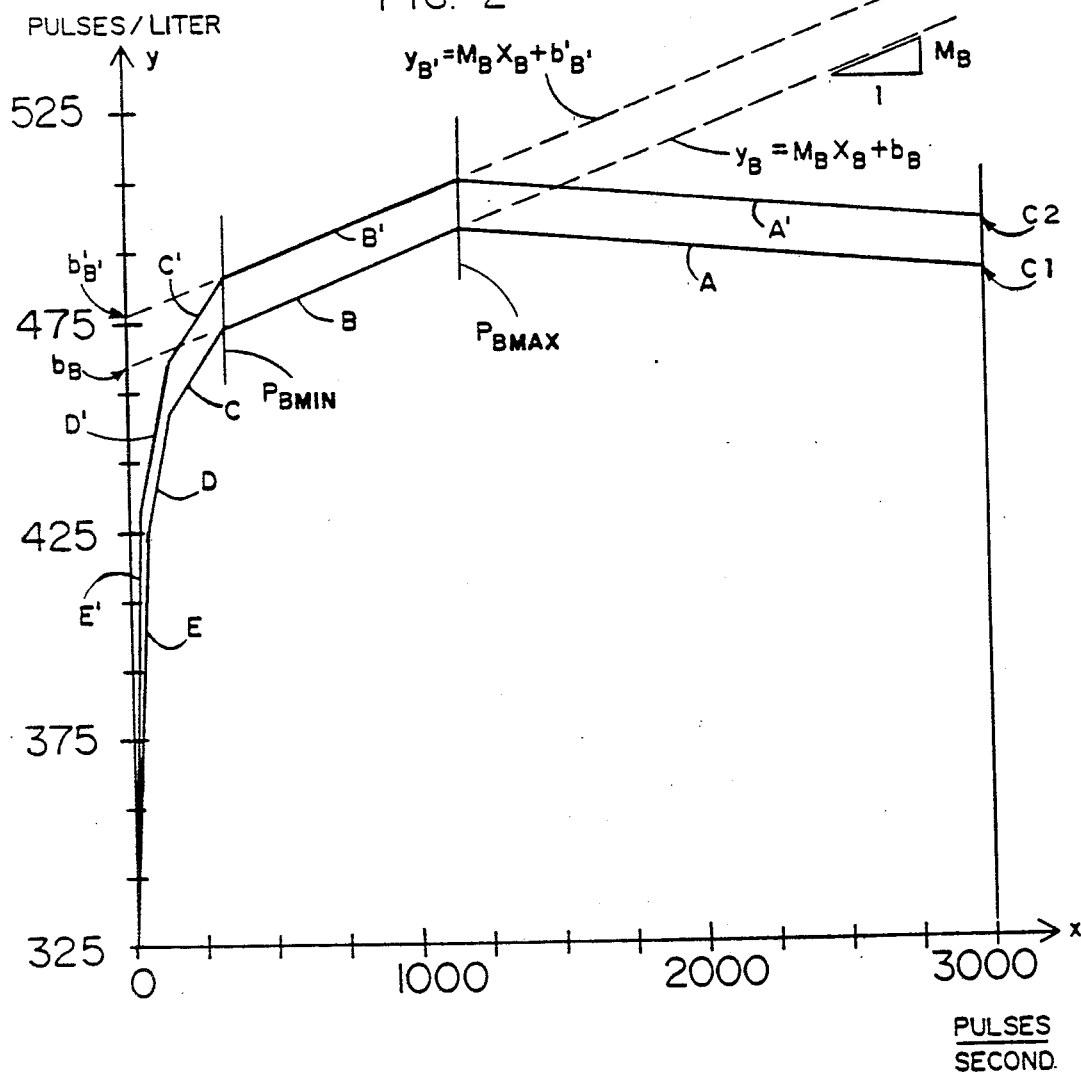
FIG. 2 is a graph showing a piecewise linear approximation of the operating characteristic of the gas turbine of FIG. 1.

In the preferred embodiment of the present invention, these three delivery rates correspond to segments A, B and C of the piecewise linear approximation of the turbine characteristic of FIG. 2. This correspondence greatly facilitates the process of providing calibration data to the instrument for each of linear segments A, B and C and thereby enabling it to accurately determine the volumes of gas which are delivered to it at the rates that are associated with those linear segments. The manner in which turbine data produced at these different delivery rates are used to calibrate the instrument will be described later in connection with operation of electronic control unit 20.

Figure 5:
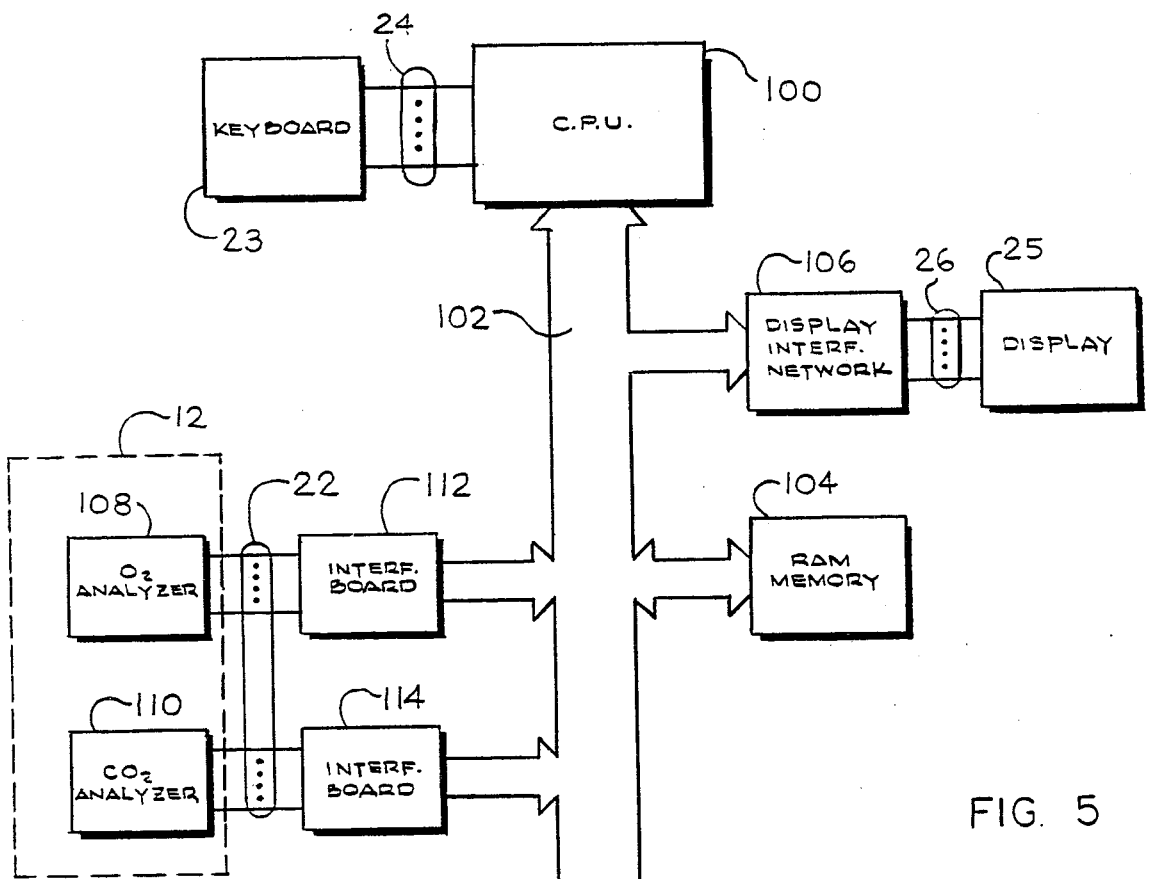
FIG. 5 is a block diagram of the electronic control unit of FIG. 1, and FIGS. 6a, b and c together comprise a flow chart that depicts the sequence of operations that are performed by the control unit of FIG. 5 during volume calibration.
Figure 5:
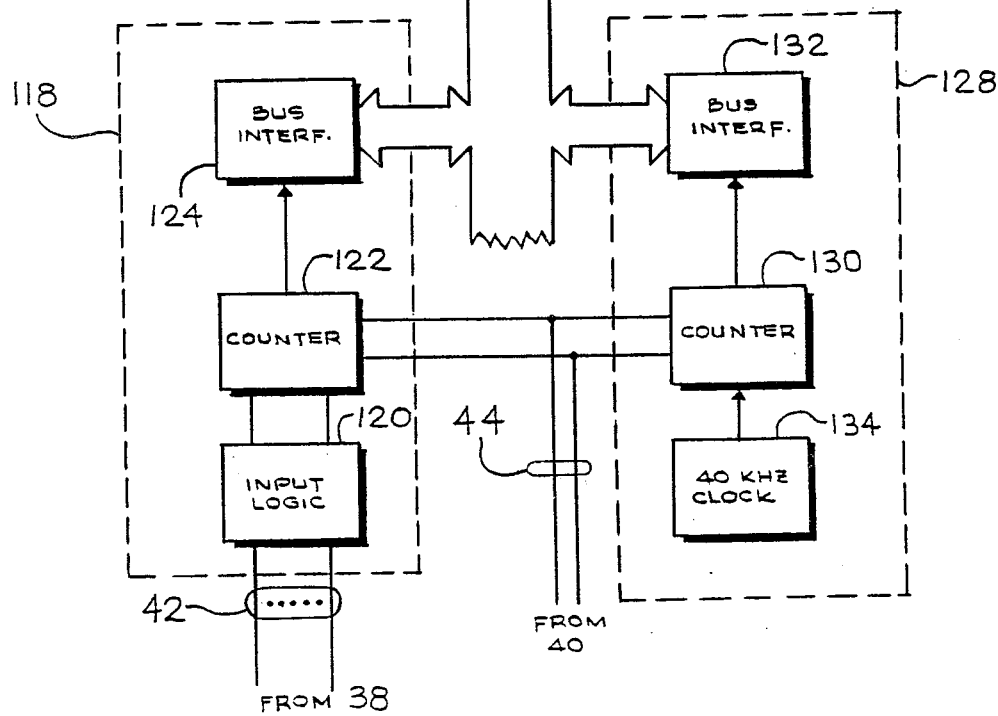

Referring to FIG. 5, there is shown a block diagram of the contents of control unit 20, those elements which appear in both FIGS. 1 and 5 being similarly numbered. As shown in FIG. 5, control unit 20 includes a central processor unit or CPU 100 which may be of any of a number of different commercially available types such as, for example, an LS-4800 board manufactured by Beckman Instruments, Inc. Generally speaking, CPU 100 includes the usual arithmetic-logic unit (ALU), a program memory, preferably stored in read-only memory (ROM), a plurality of working registers, preferably comprising random access memory (RAM) and suitable clock drive circuitry. Because the present invention may be understood without reference to the internal operation and circuitry of CPU 100, the internal operation and circuitry thereof will not be described in detail herein.

CPU 100 communicates with the various circuit networks with which it operates through a system bus 102 which may also be of a known type, such as the well-known "multi-bus". This bus carries a number of different signals such as command signals from CPU 100, status signals to CPU 100, and data signals both to and from CPU 100, all such signals being coded in multi-bit digital form. CPU 100 is also connected to keyboard 23 through conductors 24 and a CPU input/output port (not shown) which is available for that purpose on the abovementioned LS-4800 board. Alternatively, keyboard 23 may be connected to CPU 100, through bus 102, provided that a suitable bus interface network is present.

Among the devices which communicate with CPU 100 over bus 102 is a random access memory (RAM) 104 which serves as bulk read-write storage for unit 20, and a display 25 through which CPU 100 may communicate information to an operator, the display being coupled to bus 102 through a suitable display interface network 106 of a conventional type. It will be understood that the term "display" is used herein in its broad sense to refer to any device by means of which information may be communicated to an operator in human readable form and includes, for example, alphanumeric displays of the LED or LCD types, cathode ray tubes and printers.

Also connected to bus 102 is gas analysis section 12 of FIG. 1. As shown in FIG. 5, analysis section 12 may include one or more separate gas analyzers, such as oxygen analyzer 108 and carbon dioxide analyzer 110, which may be coupled to bus 102 through respective interface boards 112 and 114. Because these gas analyzers and interface boards operate in a manner known to those skilled in the art to supply gas concentration information to bus 102 on command, the internal structure and operation thereof will not be described in detail herein.

Also connected to bus 102 are gas flow sensing networks 118 and 128 through which CPU 100 receives turbine and breath switch data over conductors 42 and 44. Of these gas flow sensing networks, network 118 is adapted to supply to CPU 100, via bus 102, a number indicative of the total number of pulses produced by turbine 38 between the opening and closing of breath switch 40. To the end that this may be accomplished, network 118 includes a suitable input circuit 120 for logically OR-ing the multi-phase signals produced by the various LED phototransistor pairs within turbine 38 into a single pulse train, a counter 122 for counting the number of pulses produced by input circuit 120 and a conventional bus interface network 124 for supplying the contents of counter 122 to CPU 100 upon command. The counting activity of counter 122 is coordinated with the state of breath switch 40 by applying the output of breath switch 40 thereto as an enable signal, via conductors 44. After counter 122 communicates to CPU 100 the total number of turbine output pulses, it is preferably reset by an appropriate command from CPU 100.

Breath duration information from breath switch 40 is provided to CPU 100 by gas flow sensing network 128 which may include a counter 130, a bus interface network 132 and a fixed frequency clock 134 having a frequency of, for example, 40 KHz. Like counter 122, counter 130 is enabled by the signal on conductors 44 when breath switch 40 is open. During the time that it is enabled, counter 130 counts the pulses received from clock 134 and stores the same until CPU 100 requests the same through bus interface network 132. After this information has been supplied to CPU 100, counter 130 is preferably reset by an appropriate command from CPU 100 in preparation for the next operation of breath switch 40. Because counter 130 counts pulses having a fixed frequency, the number stored in counter 130 during a breath is indicative of the duration of that breath.

In summary, flow sensing network 118 supplies to CPU 100 the total number of output pulses produced by turbine 38 during each operation of breath switch 40. During calibration this number is equal to the number of pulses produced during an ejection stroke of syringe 50'. In addition, flow sensing network 128 supplies to CPU 100 a number indicative of the length of the time period during which breath switch 40 was open. During calibration this number is indicative of the duration of an ejection stroke of syringe 50'. Together, these numbers allow CPU 100 to generate an actual flow rate signal, preferably in terms of a pulses-per-second value, that is associated with each stroke of syringe 50'. In accordance with the invention the availability of the latter information for a plurality of calibration gas flow rates makes it possible to calibrate the instrument of FIG. 1 over substantially the entire operating range of the turbine, and thereby enables the instrument to later determine the actual volume of sample gas delivered, in spite of changes in the sample gas flow rate.

Referring to FIG. 2, "curve" C1 represents a piecewise linear approximation of the nonlinear characteristic of a typical turbine of the class of turbines to which turbine 38 belongs. As used herein, the term "piecewise linear approximation" refers to a set of linear segments which together approximate a continuous curve. Line segments A-E of FIG. 2, for example, approximate respective curvilinear sections of the continuous curve (not shown) that characterizes the response of a typical turbine of the class of turbines to which turbine 38 belongs. The number of linear segments included in curve C1 may, in general, have any value. For practical reasons, however, the number of piecewise linear segments is preferably as small as is possible in view of the desired volume correction accuracy. It will therefore be understood that the five linear segments A-E shown in FIG. 2 represent a reasonable compromise value which affords both accuracy and ease of use.

In FIG. 2 the horizontal axis indicates the rate of flow of a breath through the turbine, and is scaled in terms of the pulses-per-second value that is associated with a particular breath. The vertical axis indicates the total number of pulses produced by the turbine per unit volume of breath at the indicated flow rate. Because the volume of the calibration syringe has a known fixed value, the unit of volume of breath will also be fixed during calibration. From the shape of typical turbine characteristic curve C1, it is apparent that the number of pulses produced per ejection stroke of syringe 50' can have a number of different values, depending upon the flow rate that is associated with that ejection stroke, i.e., depending upon the speed of piston 54 during that ejection stroke.

Prior to the present invention it was the practice to deal with the nonlinear response of a turbine by directing a flow of bias gas therethrough. This bias gas flow caused all turbine output data to be associated with a relatively horizontal region of curve C1, such as the region corresponding to linear segment A. In addition to being a relatively costly way of dealing with the non-linear response of a turbine, the use of a bias gas flow introduced new inaccuracies as a result of the fact that the chosen region was only approximately horizontal and the fact that the characteristics of a turbine change with time and the accumulation of dirt.

In accordance with one feature of the present invention, the need for a bias gas flow is eliminated by storing a complete piecewise linear approximation C1 of the response of a representative turbine within control unit 20, preferably in a ROM in CPU 100. In addition, in accordance with another important feature of the present invention, this stored characteristic is combined with actual turbine data taken during calibration to produce a second piecewise linear approximation C2 of the response of the actual turbine in its then current condition. The latter approximation is also stored within control unit 20, preferably (but not necessarily) in RAM 104, for use in interpreting flow rate signals that are received during subsequent measurements on a test subject. In this manner, instrument 10 is able to accurately determine the volume of a breath in spite of changes in the rate of flow thereof. The manner in which curve C2 is produced will be described presently. Before doing so, however, it is helpful to first discuss the form in which a curve such as curve C1 is stored, and the manner in which it can be used in making breath volume determinations.

In order to make the most efficient possible use of memory, curve C1 is stored in the ROM of CPU 100 by storing therein the maximum and minimum pulses-per-second values that are associated with each of line segments A-E of FIG. 2 (such as $P_{BMAX}$ and $P_{BMIN}$ for segment (B), along with the equations of the line segments that apply between those values. These latter equations are preferably stored by storing the parameters of these equations as expressed in slope-intercept form, i.e., in the form $y = mx + b$, where y is the vertical axis variable, x is the horizontal axis variable, m is the slope of the line and b is the y axis intercept. This form of storage allows each line segment to be uniquely specified in terms of only four stored values, namely $P_{MAX}$, $P_{MIN}$, m and b. Naturally, the equations for these line segments may also be stored in other well-known forms, such as the "point-slope" form or the "two-point" form, if desired.

As pulses-per-second data for a breath is derived from the output signals of turbine 38 and breath switch 40, it is compared with the maximum and minimum pulses-per-second values of each line segment until the segment along which it lies is identified. The pulses-per-second value may then be substituted into the equation for the line segment, which is then solved to provide the pulses-per-liter value which corresponds to the measured pulses-per-second value. Once the pulses-per-liter value is available, volume data for the breath may be provided in one of two forms. On the one hand, the pulses-per-liter value may be divided into the total number of pulses to yield a volume value in liters. Alternatively, the pulse-per-liter value may be divided into the pulses-per-second value to produce volume data in the form of a volume rate of flow in liters per second. Note that volume rate of flow in liters-per-second need only be multiplied by the duration of a breath to yield the volume of a breath in liters. Since one or both of these determinations may be made for any point on curve C1, it will be seen that the storage and use of curve C1 allows the volume data for a breath to be determined in spite of changes in regard to the rate at which that breath is delivered. This in turn allows the instrument as a whole to correctly interpret the output data from the gas analyzers of gas analysis section 12. Because the manner in which each of the above-described comparisons and algebraic manipulations may be performed is well known to programmers, the specific steps that are followed by CPU 100 in performing the same will not be described in detail herein.

While the above-described volume determination takes into account the nonlinearity of a typical turbine, it does not take into account the differences between a particular turbine and a typical turbine of the same type. In accordance with an important feature of the present invention, there is provided a calibration method and apparatus whereby stored curve C1 of FIG. 2 and the pulses-per-second data that is received for a plurality of gas flow rates during calibration are combined to produce and store a corrected curve C2 that reflects the actual properties of the particular turbine in its then-current operating condition. This corrected curve may then be used in the above-described manner to provide gas volume data which the instrument can use to provide gas concentration readings having an accuracy which far surpasses that available from respiratory instruments that were available prior to the present invention. The manner in which corrected curve C2 is produced during calibration will now be described.

Generally speaking, the information necessary to generate curve C2 is produced during calibration by using syringe 50' to produce turbine output data at flow rates that correspond to at least the most frequently used ones of line segments A-E of curve C1 of FIG. 2. In the preferred embodiment, this turbine output data is produced without the need for a costly mechanical device for driving piston 54. This is accomplished by communicating to an operator, through display 25, the information necessary for the operator to manually stroke syringe 50 at the speeds which will result in the desired pulses-per-second values from turbine 38.

More particularly, after control unit 20 has been placed in its calibration mode, it outputs a message to the operator requesting him to stroke syringe 50' so that it may receive turbine output data for a first line segment such as segment A' of curve C2. If the stroke is too fast or too slow, control unit 20 will reject the resulting data and request the operator to repeat the stroke at a faster or slower rate. This process is repeated until sufficient information for the first linear segment has been received. Control unit 20 then requests the operator, through display 25, to change the syringe setting and stroke the syringe so that it may receive turbine output data for another line segment such as segment B' of curve C2. Again the control unit accepts only data resulting from strokes of the proper speed and informs the operator whether unacceptable strokes are too fast or too slow. This process is then repeated for the desired number of additional line segments.

Once the operator has entered sufficient turbine data for each of the desired line segments, this data is used to generate a set of correction factors which, in effect, determine new intercepts for the equations of the line segments of curve C1. These new intercepts, together with the stored slopes of the line segments of curve C1, define a corrected piecewise linear approximation C2 which reflects the response of the actual turbine being used. The latter is then stored for use by control unit 20 in interpreting the volume of gas delivered during all subsequent measurements, i.e., until the next volume calibration. The result is an instrument which is accurately volume calibrated not only in view of the nonlinearity of the gas turbines generally, also in view of the individual characteristics of the actual turbine being used.

Figure 6A:
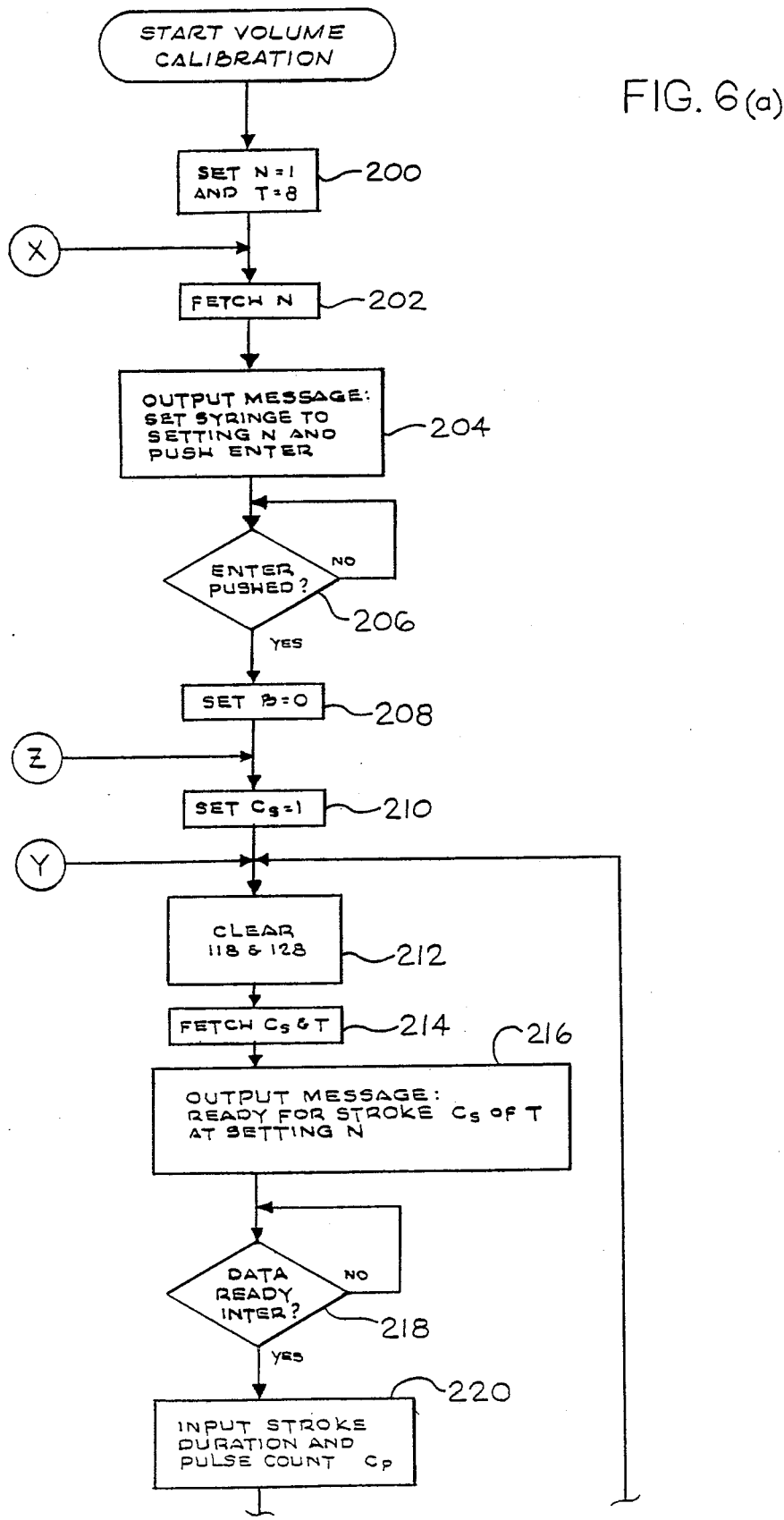
Figure 6B:
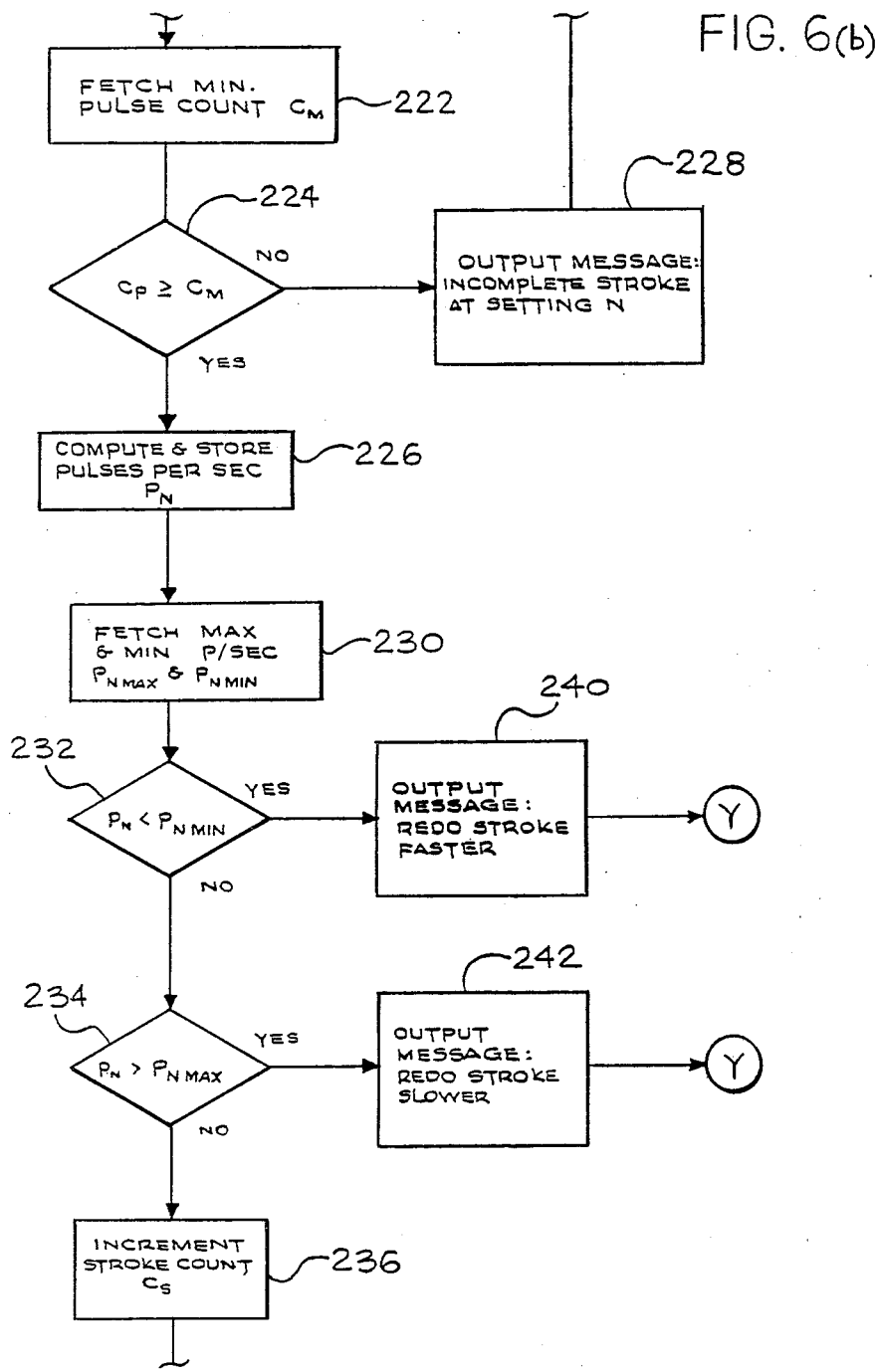

The manner in which the present invention operates to accomplish the above-described results is most easily understood in connection with the flow chart of FIGS. 6a-c. The meanings of the various symbols used in this flow chart are as follows:

| Symbol | Meaning |
| --- | --- |
| N — | N is a variable that identifies the linear segment of curve C1 or C2 for which turbine data is being received, and the syringe setting (position of control plate 80) that is associated with that segment. |
| B — | B is a variable that represents the number of times an operator has attempted to produce an acceptable set of strokes at setting N of the syringe. |
| $C_s$ — | $C_s$ is a variable representing the number of acceptable syringe strokes which have been made by the operator at setting N. |
| T — | T is a constant that indicates the total number of acceptable syringe strokes which are necessary to fix the position of one line segment of curve C2. |
| $C_p$ — | $C_p$ is the total number of pulses produced by turbine 38 during an ejection stroke of the syringe. |
| $C_m$ — | $C_m$ is a constant representing the minimum number of pulses which must be produced by turbine 38 during a stroke in order for the stroke to be considered an acceptable one. |
| $P_N$ — | $P_N$ is the pulses-per-second value resulting from an ejection stroke of the syringe at setting N. |
| $P_{Nmax}$ — | $P_{Nmax}$ is a constant indicating the maximum acceptable pulses-per-second value at setting N; this value corresponds to the upper endpoint of one of the line segments of curves C1 and C2. |
| $P_{Nmin}$ — | $P_{Nmin}$ is a constant that indicates the minimum acceptable pulses-per-second value at setting N; this value corresponds to the lower end of one of the line segments of curves C1 and C2. |
| A — | A is a variable representing the number of times that a loop has been traversed. |
| $C_v$ — | $C_v$ is a variable representing the coefficient of variation of a set of strokes at a particular setting, that is, the standard deviation of the pulses-per-second values of the strokes divided by the mean pulses-per-second value thereof. |
| $F_{cN}$ — | $F_{cN}$ is a correction factor which specifies the position of a line segment of curve C2 with respect to the position of the corresponding segment of curve C1; a correction factor will exist for each setting of N. |

The flow chart of FIGS. 6a-c will now be described. Upon entering the volume calibration sequence and encountering block 200, CPU 100 sets N=1 to select a first line segment such as A' (i.e. a first gas flow rate) for which to receive turbine data. CPU 100 also sets T=8, indicating that 8 acceptable strokes are necessary to fix the position of segment A'. The set value of N is used in blocks 202 and 204 to output to the operator, on display 25, the message "set syringe to setting 1 and push enter". CPU 100 then enters a wait loop, indicated by block 206, which is exited when the operator makes the requested syringe setting and pushes the enter button on keyboard 23. After CPU 100 exits this wait loop, it sets variable B=0, as indicated by block 208, and sets variable $C_s$=1, as indicated by block 210. Upon encountering block 212, CPU 100 clears flow sensing networks 118 and 128 of FIG. 5 to prepare the same for the receipt of data from the turbine 38 and breath switch 40. After these networks are cleared, CPU 100 fetches the current values for Cs and T and outputs to the operator the message "ready for stroke 1 of 8 at setting 1", as indicated by blocks 214 and 216. This informs the operator that the instrument is ready for the first stroke of syringe 50' and that eight acceptable strokes are necessary to gather sufficient data to fix the new position of line segment A'. The instrument then waits in this condition, as indicated by block 218, until a data ready interrupt signal indicates that a stroke has actually been made.

When the ejection stroke does occur, CPU 100 will input the stroke duration and pulse count $C_P$, as called for by block 220, and then fetch the minimum pulse count $C_m$ per block 222. As indicated by comparison block 224, if the actual pulse count value $C_p$ is greater than or equal to the minimum value $C_m$, CPU will go on to compute and store the pulses-per-second value $P_N$ for the just-completed stroke, as indicated by block 226. If, on the other hand, actual pulse count $C_p$ is less than the minimum pulse count $C_m$, the operator will be informed of this fact by the message "incomplete stroke at setting 1", as called for by block 228. This requires the operator to repeat the stroke in a manner which will produce a higher turbine output pulse count. In addition to alerting an operator of the fact that he may not be operating the syringe between its true innermost and outermost positions, blocks 224 and 228 may be used to help identify circuit failures such as the failure of one of the LED's or phototransistors within turbine 38.

Based on the pulses-per-second value $P_N$ that is computed in block 226, CPU 100 next fetches the maximum and minimum acceptable pulses-per-second values $P_{Nmax}$ and $P_{Nmin}$ for N=1, as called for by block 230, and compares $P_N$ thereto in blocks 232 and 234 to determine if it is between them. These comparisons together assure that actual pulses-per-second value $P_N$ lies between the end points of the line segment for which calibration data is being sought. In the event that this dual test is passed, stroke count $C_s$ is incremented in block 236 and then compared against the total number of acceptable strokes that are required at setting N, as called for by block 238. If the required number of acceptable strokes has not yet been made, block 238 directs CPU 100 back to block 212, via branch connector y, to initiate a request for additional strokes.

Alternatively, if the actual pulses-per-second value $P_N$ for a particular stroke fails to fall within the range called for by blocks 232 and 234, stroke count $C_s$ is not incremented, and CPU 100 is directed to one of blocks 240 and 242. The applicable one of these blocks informs the operator whether the just-completed stroke was unacceptable as a result of being too fast or as a result of being too slow. In either case, CPU 100 is returned to block 212, via branch connector y, to call for another stroke.

The above-described stroke entry sequence is repeated as necessary until the actual number of acceptable strokes is equal to the required number of strokes; in the present example this number is (T+1) since $C_s$ was initially set to 1 in block 210. When the required number is reached, comparison block 238 directs CPU 100 to block 244 to clear a counter A which will be described presently. Thereafter, as called for by block 246, CPU 100 calculates the coefficient of variation $C_V$ of the pulses-per-second values for the accepted strokes by calculating the standard deviation thereof and dividing the same by the mean value thereof (a calculation that is familiar to those skilled in the art) and fetches the maximum acceptable value for $C_V$, $C_{Vmax}$.

If $C_v$ is greater than the maximum acceptable value therefor $C_{vmax}$, the desired flow of the program is interrupted as block 248 directs CPU 100 to a block 252. In the latter block CPU 100 increments counter A, and then proceeds to a comparison block 254 which compares the value of A to a test value, in this case 2. If the content of counter A is not equal to 2, CPU 100 is directed to block 256, which calls for the deletion of the pulses-per-second values for the two strokes that are furthest from the mean value of $P_N$. CPU 100 is then returned to block 246 to compute a new value for $C_V$. This in effect gives the instrument a second chance to find an acceptable set of pulses-per-second values among the values produced by the operator at syringe setting N.

If, however, the program attempts to reach block 256 a second time, i.e., attempts to delete data for two further strokes, it will be prevented from doing so by comparison block 254, which then directs CPU 100 to a further block 258. As a result of encountering block 258, a counter B is incremented to signal the fact that, after two attempts to compute an acceptable $C_V$ value, CPU 100 was unable to do so. Under the latter condition, CPU 100 is directed to comparison block 260 which, unless counter B has a value of three, reaches block 262 which, in turn, causes the operator to be informed that it is necessary for him to re-enter the entire sequence of strokes at setting N. Following the outputting of this information, the program re-enters the stroke entry sequence at block 210 via branch connector Z.

In those rare instances in which three complete sets of acceptable strokes at setting N fail to result in an acceptable coefficient of variation, then comparison block 260 will respond to the 3 in counter B to direct CPU 100 to a block 264. The latter block causes CPU 100 to inform the operator that he should consult the user's manual because of the probability of a failure within the instrument. Once this fault is corrected, the operator may then restart the calibration sequence at block 200 and repeat the process to establish an acceptable set of values for the coefficient of variation for each syringe setting.

Returning to the desired flow of the calibration sequence at block 248, if coefficient of variation $C_V$ is less than or equal to $C_{Vmax}$, comparison block 248 will cause CPU 100 to proceed to block 250. In the latter block CPU 100 is caused to calculate a correction factor (in a manner that will be described presently) and thereby determine the position of the segment of interest of curve C2 with respect to the corresponding segment of curve C1. After the calculation of the correction factor $F_{CN}$ for setting N=1, CPU 100 is directed to a comparison block 270 which compares the then current value of N with the desired maximum value thereof. If the value of N is not equal to the maximum value (in the preferred embodiment 3), CPU 100 is directed to a block 272 which increments N and returns CPU 100 to block 202 via branch connector X. This causes CPU 100 to request turbine data for another syringe setting so that it may determine the position of a new line segment on curve C2, such as segment B'. When this occurs, the above-described stroke entry sequence will be repeated for the new syringe setting.

When correction factors have been produced for each of the desired number of line segments of curve C2, CPU 100 is directed to block 274. This block causes CPU 100 to calculate the intercept values $b'_N$ for each line segment of curve C2. The latter intercepts, together with the stored slopes of the line segments of curve C1, provide the m and b values that are necessary to complete the slope-intercept form equations for the line segments of curve C2. As will be explained in greater detail presently, these calculations involve the multiplication of the intercepts for the line segments of curve C1 by their respective correction factors. Block 274 is followed by block 276 which causes CPU 100 to actually generate and store the slope-intercept firm equations which together define piecewise linear curve C2. Once the latter curve is stored, the volume calibration sequence is complete; CPU 100 is then in condition to proceed with unrelated calibration procedures, such as zeroing, or with the taking of actual measurements.

The manner in which the correction factors are calculated for the line segments of curve C2 will now be described. Referring to FIG. 2, it will be seen that line segment B of curve C1 comprises that portion of a line $y_B = m_B x_B + b_B$ which lies between pulses-per-second values $P_{Bmax}$ and $P_{Bmin}$. The latter equation is in the previously mentioned slope/intercept form in which $m_B$ represents the slope of the line and $b_B$ represents the intercept of that line on the vertical or Y axis. The graphical significance of $m_B$ and $b_B$ are shown on the dotted line extension of curve B of FIG. 2 The correction factor $F_{CB}$ for segment B is that number which, when multiplied by intercept $b_B$ of curve C1, yields the value of the intercept $b'_{B'}$ of line segment B' of curve C2. This relationship is expressed in equation (1) of FIG. 2. The corrected intercept $b'_{B'}$ together with slope $m_B$ (which may reasonably be assumed to be the same for curves C1 and C2) is sufficient to specify the equation for line segment B' of curve C2 between maximum and minimum pulses-per-second values $P_{Bmax}$ and $P_{Bmin}$.

From the foregong it will be seen that correction factor $F_{CB}$ is a number which, in effect, allows line segment B of curve C1 to be shifted up or down to a new position in which it more nearly reflects the response of the actual turbine in its then current condition. The correction factors $F_{CA}$ and $F_{CC}$ for line segments A and C will be understood to operate in a similar manner to shift those line segments to new positions in which they also reflect the operation of the turbine in its then current condition.

Referring to equation (2) of FIG. 2, there is shown the algebraic expression that is used to calculate correction factors such as $F_{CB}$. In equation (2), $P_{Bmeas}$ is the average pulses-per-liter value that is associated with an acceptable set of turbine output data taken with the syringe at a setting such as B. $P_{Bcalc}$ is the pulses-per-liter value, from curve C1, which is associated with the average of the measured pulses-per-second values. Equation (2) simply combines these two numbers to produce a scaling factor that allows any point on line segment B' of curve C2 to be expressed in terms of the corresponding point on line segment B of curve C1.

In operation, the calculation called for by equation (2) is carried out by CPU 100 each time that it encounters block 250 of FIG. 6c. Once CPU 100 has encountered block 250 once for each line segment for which a correction factor is required, i.e., once all of the correction factors are available the latter may be combined with the previously stored intercepts of the respective line segments of curve C1 in accordance with equation (1), as CPU 100 encounters block 274 of FIG. 6c. Finally, as CPU 100 encounters block 276, these intercepts may be combined with the previously stored respective slope values to produce and store the parameters of the equations for curve C2. Alternatively, the correction factors alone may be stored for use in generating the equations for the line segments of curve C2 from those of curve C1 on an as-needed basis. In particular, when an equation for a segment of curve C2 is needed, it may be produced by multipying the intercept of the equation for the corresponding segment of Curve C1 by the applicable correction factor. The advantage of the latter approach is that fewer memory locations are required to store the information necessary to make the desired piecewise linear approximation available to the instrument. The two approaches to storing the piecewise linear approximation are equivalent, however, since both can be used in the above-described manner to interpret the gas concentration measurements made by gas analysis section 12.

The intercepts of piecewise linear segments A, B and C are in general sufficiently different from one another that it is desirable to have independently determined correction factors for use in fixing the intercepts of line segments A', B' and C'. For the steepest piecewise linear segments, such as D and E, however, it is possible to use the same correction factor that was determined in connection with line segment C, without a significant loss of accuracy. This application of the correction factor for line segment C to line segments D and E is desirable because it makes unnecessary either the use of a separate calibration syringe with a smaller volume or the use of extremely slow piston speeds. The latter approaches are nevertheless available should they be desirable in particular applications. It will therefore be understood that the present invention contemplates both embodiments in which the correction factors for all line segments are determined independently, and embodiments in which one or more correction factors are derived from measurements made for other line segments. In both cases, the instrument is made able to determine the volume of gas delivered during a breath with an accuracy that is substantially greater than that exhibited by previously available instruments.

It will be understood that since the volume calibration process described above is carried out on a regular basis, the instrument of FIG. 1 is regularly provided with a fresh nonlinear turbine characteristic curve such as C2 of FIG. 2. This assures that the instrument always has available to it information concerning the then current response of turbine 38, even as that response changes with time, wear and the accumulation of dirt. Thus, the benefits of the invention are available on a continuing basis.

In view of the foregoing, it will be seen that the volume calibration method and apparatus of the invention includes both improvements in the apparatus for delivering calibration gas (the syringe) and in the method and apparatus for using that gas to volume calibrate the instrument. Together, these improvements result in an instrument which, with each calibration, reflects not only the nonlinear response of a typical turbine, but also the nonlinear response of the particular gas turbine in its then current condition. As a result, the overall accuracy of all measurements which are made with the instrument are significantly improved.

What is claimed is:

1. In a gas analysis instrument ofthe type having at least one gas analyzer for measuring the concentration of a component of interest in human breath, and a gas turbine for producing a number of output pulses that varies in accordance with the volume and rate of flow of human breath therethrough, the improvement comprising:
  (a) first means for storing a piecewise linear approximation of the response of the gas turbine,
  (b) second means responsive to the number of output pulses produced by the turbine for determining the operating point of the turbine on the stored approximation, and
  (c) third means responsive to the stored approximation and the output of the second means for providing volume data for a breath.

2. The instrument of claim 1 in which the first means stores the piecewise linear approximation by storing the parameters of the equations for a plurality of linear segments, together with the maximum and minimum values between which respective linear segments are applicable.

3. The instrument of claim 2 in which the approximation gives the number of pulses-per-liter produced by the turbine as a function of the number of pulses-per-second produced thereby.

4. The instrument of claim 3 in which the second means determines said operating point by dividing the total number of turbine output pulses by the time interval during which those pulses occurred to produce a pulses-per-second value.

5. The instrument of claim 4 in which the third means includes (a) means for comparing the pulses-per-second value with said maximum and minimum values to identify the applicable linear segment, (b) means for combining the pulses-per-second signal with the respective linear segment to determine the associated pulses-per-liter value, and (c) means for determining the volume of a breath from said pulses-per-liter value.

6. The instrument of claim 4 in which the third means includes (a) means for combining said pulses-per-second value with the stored approximation to produce a pulses-per-liter value, and (b) means for combining said pulses-per-second value with said pulses-per-liter value to determine the liters-per-second value for a breath.

7. The instrument of claim 1 in which the linear approximation gives the number of pulses-per-liter produced by the turbine as a function of the number of pulses-per-second produced thereby.

8. The instrument of claim 7 including a breath switch connected in series with the gas turbine to produce a signal indicative of the duration of a breath.

9. The instrument of claim 8 in which the second means includes a counter for counting the output pulses produced by the turbine, said counter being enabled by the breath duration signal from the breath switch.

10. The instrument of claim 9 in which the second means includes means for dividing the number of output pulses produced during a breath by the duration of that breath to produce a pulses-per-second value for use in determining said operating point.

11. The instrument of claim 10 in which the third means includes means for determining a pulses-per-liter value from said pulses-per-second value and the stored approximation, and means for combining said pulses-per-liter value with said pulses-per-second value to determine the liters-per-second value for a breath.

12. In a gas analysis instrument of the type having at least one gas analyzer for measuring the concentration of a compound of interest in human breath, and a gas turbine for producing an output signal that varies in accordance with the volume and rate of flow of breath therethrough, the improvement comprising:
  (a) first means for storing the information necessary to make available a piecewise linear representation of the response of the gas turbine, said representation relating the volume of breath flowing through the turbine to the rate of flow of that breath therethrough,
  (b) a breath switch connected in series with the gas turbine to generate an output signal indicative of the duration of a breath,
  (c) second means responsive to the output signal of the turbine and the output signal of the breath switch for determining the rate of flow of a breath, and
  (d) third means responsive to the first means and the second means for determining volume data for a breath.

13. The instrument of claim 12 in which the first means stores the piecewise linear representation by storing the parameters of the equations for a plurality of line segments, together with the ranges of flow rates over which those line segments are applicable.

14. The instrument of claim 13 in which the third means determines the volume data for a breath by (a) substituting into one of said equations the rate of flow determined by the second means, and (b) solving said equation for said volume data.

15. The instrument of claim 12 or 14 in which the output signal of the turbine comprises a series of pulses and in which the second means includes (a) a counter for counting the number of pulses produced by the turbine during the time that the breath switch is open, and (b) means for dividing the number in said counter by the time that the breath switch is open to determine the rate of flow of a breath.

16. The instrument of claim 12 including means for storing the information necessary to make available a second piecewise linear representation of the response of an average turbine of the class of turbine to which the gas turbine belongs.

17. The instrument of claim 16 in which the stored piecewise linear representation is derived from the second piecewise linear representation on the basis of volume data taken during calibration.

18. The instrument of claim 12 in which the volume data is the volume of a breath.

19. The instrument of claim 12 in which the volume data is the volume rate of flow of a breath.

20. A method for volume calibrating a gas analysis instrument of the type having (a) a source for providing a known volume of calibration gas, and (b) a gas turbine for providing an output signal that varies in accordance with the volume and rate of flow of gas therethrough, said method including the steps of:
  (a) storing a first piecewise linear approximation of the output response of a typical turbine of the class of turbine to which said gas turbine belongs,
  (b) directing said known volume of gas through the turbine at a plurality of rates of flow which correspond to a plurality of the linear segments of the piecewise linear approximation and storing data indicative of the resulting turbine output signals,
  (c) combining the approximation of step (a) with the data stored during step (b) to produce a second piecewise linear approximation of the output response of the gas turbine, and
  (d) making the second piecewise linear approximation available for use in interpreting measurements made by the instrument.

21. The method of claim 20 in which the first stored approximation gives the volume of gas flowing through the turbine as a function of the rate of flow of gas therethrough.

22. The method of claim 20 or 21 in which the first stored approximation is stored by storing the parameters of the equations for a plurality of linear segments, together with the ranges of flow rates over which those linear segments are applicable.

23. The method of claim 22 in which the second approximation is produced by changing the parameters of the equations of the linear segments of the first approximation to reflect the data received during step (b).

24. The method of claim 23 in which the data associated with a flow of said known volume of gas through the turbine is accepted for use in producing the second piecewise linear approximation only if the flow rate associated therewith is within a predetermined range of acceptable flow rates.

25. The method of claim 20 in which said known volume of gas is directed through the turbine a plurality of times at each flow rate, and in which said stored data is averaged before being used in producing the second approximation.

26. The method of claim 20 in which the turbine produces an output signal comprising a succession of pulses, and in which the first linear approximation relates the number of pulses per unit volume of gas flow to the number of pulses-per-second of gas flow.

27. The method of claim 26 in which the position of a linear segment of the second linear approximation is determined by (a) measuring the pulses per unit volume that result from the flow of said known volume of gas through the turbine, (b) dividing the total number of pulses that result from the flow of said known volume of gas through the turbine by the duration of said flow to determine a pulses-per-second value, (c) calculating a correction factor from the measured number of pulses per unit volume and the number of pulses per unit volume called for by the first linear approximation at the same pulses-per-second value, and (d) applying said correction factor to one of the linear segments of the first linear approximation to position the corresponding linear segment of the second linear approximation.

28. In a gas volume calibration apparatus for a gas analysis instrument of the type including (a) a source for supplying a known volume of calibration gas, (b) a gas turbine for providing an output signal that varies in accordance with the volume and rate of flow of gas therethrough, and (c) a control circuit connected to the turbine, the improvement characterized by: (a) means in the control circuit for storing a first piecewise linear approximation of the response of a typical turbine of the class of turbine to which the gas turbine belongs,
  (b) means in the control circuit for receiving the output signal of the gas turbine as said known volume of gas is directed therethrough at rates of flow that correspond to at least two different linear segments of the piecewise linear approximation, and
  (c) means in the control circuit for modifying said first piecewise linear approximation in accordance with the output signals produced by the turbine during calibration to produce a second piecewise linear approximation of the response of the gas turbine.

29. The calibration apparatus of claim 28 in which the first linear approximation relates the volume of gas flowing through the turbine to the rate of flow of gas therethrough.

30. The calibration apparatus of claim 28 in which the turbine produces an output signal comprising a succession of pulses, and in which the first and second linear approximations relate the pulses-per-liter values for gas flow through the turbine to respective pulses-per-second values.

31. The calibration apparatus of claim 30 in which the first and second linear approximations are stored by storing the parameters of the equations for a plurality of linear segments, together with the ranges of pulses-per-second values associated with those linear segments.

32. The calibration apparatus of claim 31 in which the parameters of the equations of at least one of the linear segments of the second linear approximation are produced by combining the parameters of the corresponding linear segment of the first linear approximation with a correction factor that is a function of (a) the total number of pulses produced as said known volume of gas flows through the turbine, and (b) the time interval during which the latter pulses occurred.

33. The calibration apparatus of claim 28 in which the first and second linear approximations are stored by storing the parameters of the equations for a plurality of linear segments, together with the ranges of flow rates that are associated with those linear segments.

34. The calibration apparatus of claim 33 in which a parameter of at least one linear segment of the second linear approximation is derived from the parameter of the corresponding linear segment of the first linear approximation by applying a correction factor that is based on the difference between the stored response of a typical turbine and the measured response of the actual turbine.

35. In a gas volume calibration apparatus for respiratory gas analysis instruments of the type including (a) a calibration syringe having a housing and a piston slidably mounted therein, said syringe being adapted to provide a known volume of gas as the piston is moved between predetermined first and second positions, and (b) a gas turbine for providing a number of output pulses that varies in accordance with the rate at which said volume of gas flows therethrough, the improvement characterized by:
  (a) a breath switch, connected in series with the turbine, for providing an output signal indicative of the duration of a stroke of the piston,
  (b) first means for receiving the turbine output pulses produced during a stroke of the piston and the output signal of the breath switch and for generating an actual flow rate signal indicative of the speed of the stroke,
  (c) second means for storing maximum and minimum acceptable values for said flow rate signal, and
  (d) third means for comparing the actual flow rate signal with said maximum and minimum acceptable values and for accepting the actual flow rate signal for use in calibrating the instrument only if it compares favorably with said maximum and minimum values.

36. The gas volume calibration apparatus of claim 35 in which maximum and minimum acceptable values are stored for each of a plurality of stroke speeds, and in which the third means compares the actual flow rate signals for a plurality of stroke speeds with respective maximum and minimum acceptable values for those stroke speeds.

37. The gas volume calibration apparatus of claim 36 in which a predetermined number of strokes having acceptable flow rate signals must occur before the instrument is calibrated at the flow rate corresponding to the respective stroke speed.

38. The gas volume calibration apparatus of claim 37 in which the flow rate values of sid predetermined number of strokes are averaged to produce an average flow rate value for use in calibration.

39. The gas volume calibration apparatus of claim 38 in which said average flow rate value, together with the volume of the calibration syringe, determine the position of a line segment that approximates the response of the turbine between said maximum and minimum acceptable values.

40. The gas volume calibration apparatus of claim 36 including an improved calibration syringe having control means for selectably controlling stroke speed.

41. The gas volume calibration apparatus of claim 40 in which the syringe includes an aperture for admitting ambient air into the region behind the trailing edge of the piston, and in which the control means limits the stroke speed of the syringe by limiting the rate at which ambient air can flow through said aperture.

42. The gas volume calibration apparatus of claim 41 in which the control means includes a plate having at least one hole which may be rotated into alignment with said aperture.

43. The gas volume calibration apparatus of claim 35, 40, 41, or 42 in which the syringe is provided with a calibration gas inlet and a calibration gas outlet that are separate from one another, and in which the arrival of the piston in said second predetermined position positively shuts off the flow of calibration gas in at least said outlet.

44. The gas volume calibration apparatus of claim 35 including means for communicating to a user the need for faster strokes if the flow rate signal for a stroke is less than said minimum acceptable value, and for communicating to a user the need for slower strokes if the flow rate signal for a stroke is greater than said maximum acceptable value.

45. The gas volume calibration apparatus of claim 35 or 44 including means for informing a user of the number of acceptable strokes that he has performed.

46. A method for providing volume calibration data to a gas analysis instrument of the type including (a) a calibration syringe for providing a known volume of gas, said syringe having a housing and a piston slidably mounted therein, and (b) a gas turbine for providing a number of output pulses that varies in accordance with the volume and rate of flow of gas therethrough, said method including the steps of:
(a) establishing a plurality of pairs of maximum and minimum acceptable pulses-per-second values corresponding to a pluraliy of flow rates for said known volume of gas through the turbine,
(b) moving the piston in a succession of strokes to cause said known volume of gas to flow through the turbine at a first estimated flow rate,
(c) calculating the pulses-per-second values associated with the strokes of step (b),
(d) comparing the resulting pulses-per-second values to a first pair of maximum and minimum acceptable pulses-per-second values,
(e) storing those pulses-per-second values which compare favorably with said first pair of maximum and minimum acceptable values for use in calibrating the instrument, and
(f) repeating steps (b) through (e) for at least a second estimated flow rate and a second pair of maximum and minimum acceptable pulses-per-second values.

47. The method of claim 46 including the step of calculating the average of the pulses-per-second values for the acceptable strokes performed at each estimated flow rate.

48. The method of claim 47 including the step of determining the coefficient of variation of the pulses-per-second values for the acceptable strokes performed at each estimated flow rate, and rejecting those acceptable values if the coefficient of variation therefor is greater than a predetermined maximum coefficient of variation.

49. The method of claim 46 including the steps of communicating to a user the need for faster strokes if the the pulses-per-second value for a stroke is less than the minimum acceptable value therefor, and of communicating to a user the need for slower strokes if the pulses-per-second value for a stroke is greater than the maximum acceptable value therefor.

50. The method of claim 46 or 49 including the step of counting the number of acceptable strokes and communicating that number to the operator after each stroke.

* * * * *